US012779155B2

(12) United States Patent
Wildhaber

(10) Patent No.: US 12,779,155 B2
(45) Date of Patent: Nov. 3, 2026

(54) TWO-STAGE BLOWER APPARATUS FOR A VENTILATOR

(71) Applicant: IMTMEDICAL AG, Buchs (CH)

(72) Inventor: Dieter Wildhaber, Azmoos (CH)

(73) Assignee: IMTMEDICAL AG, Buchs (CH)

( * ) Notice: Subject to any disclaimer, the term of this patent is extended or adjusted under 35 U.S.C. 154(b) by 844 days.

(21) Appl. No.: 18/245,085

(22) PCT Filed: Sep. 14, 2020

(86) PCT No.: PCT/IB2020/058519
§ 371 (c)(1),
(2) Date: Mar. 13, 2023

(87) PCT Pub. No.: WO2022/053856
PCT Pub. Date: Mar. 17, 2022

(65) Prior Publication Data

US 2024/0009412 A1 Jan. 11, 2024

(51) Int. Cl.
*A61M 16/00* (2006.01)
*F04D 17/16* (2006.01)
*F04D 29/28* (2006.01)

(52) U.S. Cl.
CPC ....... *A61M 16/0066* (2013.01); *F04D 17/164* (2013.01); *F04D 29/281* (2013.01)

(58) Field of Classification Search
CPC ...... F04D 17/164; F04D 17/12; F04D 17/122; F04D 29/444; F04D 29/30; F04D 29/281; A61M 16/0066
See application file for complete search history.

(56) References Cited

U.S. PATENT DOCUMENTS 3,680,978 A * 8/1972 Mercer ................. F04D 29/263 384/317
5,071,317 A 12/1991 Leach
6,543,449 B1 4/2003 Woodring et al.
(Continued)

FOREIGN PATENT DOCUMENTS

DE 3818046 C1 * 6/1989 ............... B08B 5/02
DE 100 10 077 A1 9/2001
(Continued)

OTHER PUBLICATIONS

Translation of EP 1201928 (Year: 2002).*
(Continued)

*Primary Examiner* — Victoria Murphy
(74) *Attorney, Agent, or Firm* — Secant IP, P.L.L.C.

(57) ABSTRACT

The invention relates to a two-stage blower apparatus 120 for a ventilator for providing a respiratory gas for a patient having a multi-part blower housing 121 comprising at least one first housing part 122 and a second housing part 132. A gas inlet 123 for the respiratory gas is provided on the first housing part 122 and a gas outlet 133 for the respiratory gas is provided on the second housing part 132, wherein the blower apparatus 120 comprises a first blower wheel 140 and a second blower wheel 150. The first blower wheel 140 or the second blower wheel 150 are arranged in sections in the first housing part 122 and are arranged in sections in the second housing part 132.

20 Claims, 5 Drawing Sheets

(56) References Cited

U.S. PATENT DOCUMENTS

| | | | | |
|---|---|---|---|---|
| 2003/0062045 | A1* | 4/2003 | Woodring | A61M 16/0051<br>128/204.21 |
| 2012/0266887 | A1 | 10/2012 | Daly et al. | |
| 2020/0072232 | A1* | 3/2020 | Alstad | F04D 29/329 |

FOREIGN PATENT DOCUMENTS

| | | | | |
|---|---|---|---|---|
| EP | 1 015 056 | A1 | 7/2000 | |
| EP | 1201928 | A2 * | 5/2002 | F04D 19/042 |
| EP | 2 000 675 | A2 | 12/2008 | |
| WO | 2007/009766 | A1 | 1/2007 | |
| WO | 2007/134405 | A1 | 11/2007 | |
| WO | 2013/020167 | A1 | 2/2013 | |

OTHER PUBLICATIONS

Translation of DE 3818046 (Year: 1989).*
International Search Report Corresponding to PCT/IB2020/058519 mailed Jun. 4, 2021.
Written Opinion Corresponding to PCT/IB2020/058519 mailed Jun. 4, 2021.

* cited by examiner

TWO-STAGE BLOWER APPARATUS FOR A VENTILATOR

This application is a National Stage completion of PCT/IB2020/058519 filed Sep. 14, 2020.

FIELD OF THE INVENTION

The invention relates to a two-stage blower apparatus for a ventilator according to the independent claim(s).

BACKGROUND OF THE INVENTION

In the known prior art there are various blower apparatuses for ventilators for providing a respiratory gas for a patient. Such blower apparatuses can be configured to be single-stage or multi-stage and comprise at least one blower wheel, wherein the blower wheel sucks in air or a gas mixture from the surroundings and compresses it in a gas channel. The compressed gas is supplied from the gas outlet of the gas channel directly or indirectly as respiratory gas to a patient.

DE 10 010 077 A1 discloses a suction device for dental, medical and industrial purposes having a drive motor and having a multistage radial blower driven by the drive motor. The radial blower comprises a rotor which comprises a multiplicity of blower wheels stacked axially one behind the other, which are spaced apart from one another by spacer sleeves. Conducting units are located in each case between the blower wheels. These conducting units are arranged axially nested with the blower wheels and are for their part spaced apart by spacer pieces showing as conducting walls. A suction device of similar genre is also shown in EP 1 015 056 A1.

The two-stage blower apparatus "Radial Blower U65" made by Micronel AG (CH) comprises a multi-part blower housing with a blower motor and a first housing part (https://www.micronel.com/products/u-line/). The gas channel in the multi-part blower housing is formed by three housing parts. A blower apparatus of similar genre is disclosed in WO 2007/009766 A1.

A disadvantage of these known solutions is that the gas channel for the respiratory gas is formed with the aid of many housing components, which all form a plurality of barriers for the respiratory gas during flow through the gas channel and thus bring about a reduction in the respiratory gas throughput.

SUMMARY OF THE INVENTION

It is the object of the present invention to eliminate one or more disadvantages of the prior art. In particular, a two-stage blower apparatus for a ventilator should be provided for providing a respiratory gas for a patient by means of which the respiratory gas throughput in the blower apparatus is increased.

The object is achieved by the features of the independent claim. Advantageous further developments are presented in the figures and in the dependent patent claims.

The two-stage blower apparatus according to the invention for a ventilator for providing a respiratory gas for a patient having a multi-part blower housing comprises a first housing part and a second housing part, wherein a gas inlet for the respiratory gas is provided on the first housing part and a gas outlet for the respiratory gas is provided on the second housing part. A gas channel for the respiratory gas is provided in the blower housing, which is formed in the first housing part and in the second housing part. The two-stage blower apparatus comprises a first blower wheel and a second blower wheel. The first blower wheel or the second blower wheel are arranged in sections in the first housing part and are arranged in sections in the second housing part.

A blower housing with a gas channel for the respiratory gas, wherein the gas channel is merely delimited by the first and second housing part—with respect to the surroundings outside the two-stage blower apparatus—minimizes the number of physical interfaces in the multi-part blower housing and therefore in the gas channel. Each physical interface in the gas channel contains an additional flow resistance for the respiratory gas. During compression in the two-part blower housing disclosed here in the present case, the respiratory gas in the gas channel interacts with a smaller number of interfaces and therefore with fewer flow resistances. This brings about an increase in the respiratory gas throughput and at the same time reduces the number of housing parts which delimit the gas channel with respect to the surroundings. Furthermore, the motor power of the drive motor of the blower apparatus can thus be reduced so that a lower noise evolution is produced during operation. Thus, an efficient and at the same time more cost-effective two-stage blower apparatus can be produced. The gas channel of the blower apparatus described here in the present case extends from the gas inlet to the gas outlet and leads through the two blower wheels which are arranged inside the blower housing.

Preferably the first blower wheel lies against the second blower wheel in sections. Thus, the number of interfaces in the gas channel is further reduced. Typically a spacer sleeve is located between the first blower wheel and the second blower wheel. The edges and corners present at the interfaces of the known blower apparatuses due to the production techniques bring about an additional flow resistance for the respiratory gas and force the respiratory gas to undergo turbulence. A resting of the first blower wheel on the second blower wheel in sections on one another prevents such turbulence so that the respiratory gas throughput is further increased.

Preferably a drive device is provided for driving the two blower wheels, wherein the drive device is arranged adjacent to the second housing part and has a drive shaft and at least one of the two blower wheels is arranged on the drive shaft. Thus, at least one of the blower wheels is motor-driven so that the respiratory gas can be compressed efficiently.

Preferably both blower wheels are arranged on the drive shaft so that both blower wheels are driven synchronously and the efficiency during two-stage compression is further improved.

Advantageously the at least one blower wheel is shrunk on the drive shaft. Thus, the at least one blower wheel is fixed securely in a fixed position on the drive shaft wherein the blower wheels consist of plastic, for example, of polyamide. Alternatively to shrinking on, the at least one blower wheel can be adhesively bonded or pressed onto the drive shaft. Advantageously both blower wheels are shrunk or adhesively bonded or pressed onto the drive shaft. An additional fastening component for fastening the blower wheels on the drive shaft can be dispensed with.

Preferably the two blower wheels each have at least one flow channel with a plurality of blower lamellae wherein the first blower wheel and the second blower wheel are each constructed in one piece. In contrast to the multi-part blower wheels, one-piece blower wheels have fewer interfaces which in turn can form flow resistances. The at least one flow channel forms the gas channel in the blower housing in sections. Before the appropriate use, the blower wheels should be balanced whereby typically either material is removed or material is added to the blower wheel at certain points. One-piece blower wheels are easy to balance so that when used appropriately, these have a smooth running power in the blower apparatus. Advantageously the blower wheels have a plurality of flow channels which form the gas channel through the blower housing in sections so that an improved compression of the respiratory gas takes place.

Preferably the first or the second housing part has a housing part opening wherein at least one of the two fan wheels extends through the housing part opening and the two housing parts are connected to one another. A spacer sleeve on the drive shaft between the two blower wheels can be dispensed with. Thus, the number of interfaces in the gas channel is further reduced. Alternatively to this, the two blower wheels extend through the housing part opening and rest against one another in the housing part opening. As a result, the flow resistance is minimized and the formation of turbulence in the gas channel is reduced.

Advantageously the first blower wheel and the second blower wheel form a one-piece blower wheel unit. Thus, in a two-stage blower apparatus there is no interface in the gas channel between the two blower wheels so that the respiratory gas throughput is further increased.

Preferably the first blower wheel has an inlet opening for the respiratory gas. When used appropriately, the respiratory gas is sucked from the surroundings into the gas inlet of the first housing part and guided further directly into the inlet opening on the first blower wheel. Inside the first blower wheel the respiratory gas is compressed in a first compression stage and leaves the first blower wheel at the blower wheel edges.

Advantageously, the at least one first blower wheel comprises a bottom section and a top section, wherein blower lamellae are arranged between the bottom section and the top section. Thus, the respiratory gas is efficiently compressed.

Advantageously a balancing section is provided on the first blower wheel at which the first blower wheel is balanced either by means of material removal or by means of material supply. For example, the first blower wheel has a collar on which a balancing weight can be placed and/or material can be removed by means of an auxiliary tool. Thus, the first blower wheel can be simply balanced so that an undesired evolution of noise is prevented when the blower apparatus is used as intended.

Advantageously a marking unit is provided on the first blower wheel in order to simply determine the position of the first blower wheel on the drive shaft during balancing and thus to simplify or accelerate the balancing. Furthermore, the rotational speed of the first blower wheel can be simply determined with the aid of the marking unit.

Preferably the second blower wheel is constructed identically to the first blower wheel. Thus, the blower apparatus can be produced simply and cost-effectively.

Advantageously the inlet opening of the first blower wheel has an inlet diameter which is the same size as the minimum inlet diameter of the gas inlet of the first housing part. Thus, during sucking in the respiratory gas does not impinge upon an edge or a corner on the first blower wheel so that an additional flow resistance can be prevented.

Advantageously the inlet opening of the first blower wheel is arranged on the top section so that the respiratory gas can be sucked in simply and without barriers.

Preferably the first blower wheel has a spinner which is arranged in the inlet opening of the first blower wheel. Thus, the entrance resistance of the respiratory gas during sucking in is minimized and the respiratory gas can be compressed in an improved manner in the first blower wheel. For example, the spinner is configured to be hemispherical so that the entrance resistance for the sucked-in respiratory gas is further minimized.

Advantageously the spinner has a spinner opening. The first blower wheel has a fixing section by means of which the first blower wheel is arranged on the drive shaft of the drive motor. The spinner opening enables a simple arrangement of the drive shaft on the fixing section of the first blower wheel since the excess air can flow off through the spinner opening.

In particular, a closure element is provided for closing the spinner opening so that the sucked-in respiratory gas cannot penetrate into the spinner opening and would form an undesired resistance for the sucked-in respiratory gas.

Alternatively or additionally, the drive shaft has an axial bore or a slot which opens into the spinner of the first blower wheel. The axial bore or the slot enables a simple arrangement of the drive shaft on the fixing section of the first blower wheel since the excess air can flow off.

Advantageously the second blower wheel has an inlet opening for the respiratory gas. When used appropriately, after compression the respiratory gas is pressed with the aid of the first blower wheel in the direction of the second blower wheel and guided further directly into the inlet opening on the second blower wheel. Inside the second blower wheel the already-compressed respiratory gas is compressed in a second compression stage and leaves the second blower wheel on the blower wheel edges in the direction of the gas outlet.

Advantageously the inlet opening of the second blower wheel has an inlet diameter which is the same size as the minimum inlet diameter of the gas inlet of the second housing part. Thus, during sucking-in the already-compressed respiratory gas does not impinge upon an edge or a corner on the second blower wheel so that an additional flow resistance can be prevented.

Preferably diffusor lamellae are provided, which are arranged on the second housing part and are arranged adjacent to the first blower wheel. The diffusor lamellae enable an improved guidance of the already-compressed respiratory gas away from the first blower wheel and in sections form the gas channel in the blower housing.

Alternatively to this, diffusor lamellae are provided, which are arranged on the first housing part and are arranged adjacent to the second blower wheel. The diffusor lamellae enable an improved conducting of the already-compressed respiratory gas towards the second blower wheel and form the gas channel in the blower housing in sections.

Alternatively or additionally, a diffusor with diffusor lamellae is provided which is arranged separably on the first or second housing part. According to the case of application, a separable diffusor can be configured simply and independently or individually and forms the gas channel in the blower housing in sections. Differently configured diffusor or diffusor lamellae change the flow characteristics of the compressed respiratory gas between the first and second compression stage or between the first and second blower wheel so that the respiratory gas throughput is variable. Advantageously the diffusor has a housing part opening wherein at least one of the two blower wheels extends through the housing part opening and the two housing parts are connected to one another. At least one of the two housing parts can have at least one receiving section so that the diffusor can be fixed in a fixed position and securely in the blower housing.

Preferably the first housing part and the second housing part can be connected to one another with a snap closure or a bayonet closure wherein at least on the first or on the second housing part a sealing unit is provided for the tight connection of the two housing parts. Thus, the first housing part and the second housing part can be connected to one another positively, securely and in a gas-tight manner. For example, the sealing unit is an O ring.

Preferably the gas channel has an outlet section which is arranged completely on the second housing part. The outlet section can be arranged radially circumferentially on the second housing part. Thus, an interaction of the completely compressed respiratory gas with an undesired flow resistance is prevented and a reduction of the respiratory gas throughput before the compressed respiratory gas leaves the blower apparatus is prevented. The outlet section opens into the gas outlet which typically guides the respiratory gas to the patient.

Advantageously the gas outlet for the respiratory gas is arranged at an angle between 60° and 120°, preferably 90° relative to the gas inlet for the respiratory gas on the second housing part. Thus, the respiratory gas is forced to make a radial motion in the blower housing and an improved compression and therefore an increased respiratory gas throughput is achieved.

Preferably at least one of the two housing parts is produced with the aid of an additive manufacturing method. Thus, the housing part can be produced rapidly, simply and therefore efficiently.

Alternatively or additionally, at least one of the two blower wheels is produced with the aid of an additive manufacturing method. Thus, the blower wheels can be produced in one piece and therefore efficiently. Expensive manufacturing tools such as, for example, in the field of injection moulding methods can be dispensed with.

Preferably the parts of the blower apparatus described here in the present case are produced with the aid of an additive manufacturing method. The advantages already mentioned previously are summed as a result and the number of barriers or flow resistances is minimized.

The method according to the invention for producing a blower apparatus comprises an additive manufacture of the first housing part and/or the second housing part and/or the first blower wheel and/or the second blower wheel and/or the diffusor of the blower apparatus described here in the present case. The advantages already mentioned previously are summed as a result and the number of barriers or flow resistances is minimized.

Further advantages, features and details of the invention are obtained from the following description in which exemplary embodiments of the invention are described with reference to the drawings.

BRIEF DESCRIPTION OF THE DRAWINGS

The reference list as well as the technical content of the patent claims and figures is part of the disclosure. The figures are described cohesively and comprehensively. The same reference numbers indicate the same components, reference numbers with different indices indicate functionally the same or similar components.

In the figures.

DETAILED DESCRIPTION OF THE PREFERRED EMBODIMENTS

Figure 1:
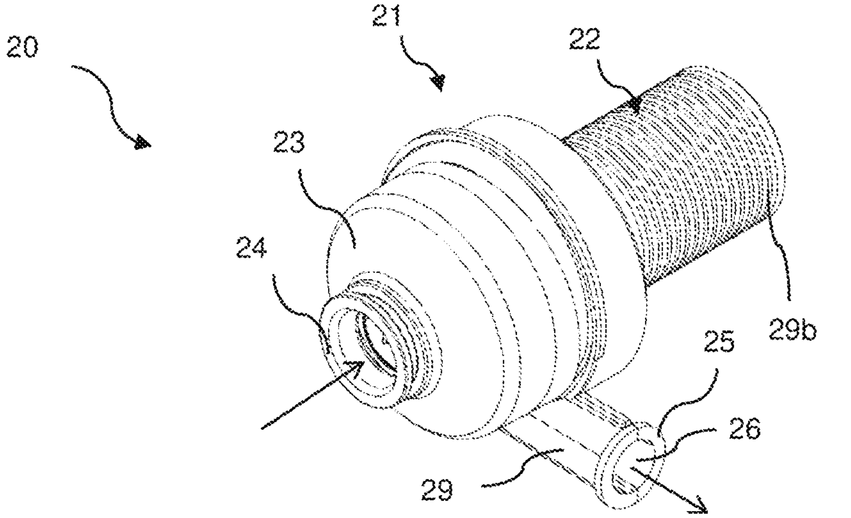
Prior Art FIG 1
FIG. 1 shows a blower apparatus with a multi-part blower housing from the known prior art in a perspective diagram.
Figure 2:
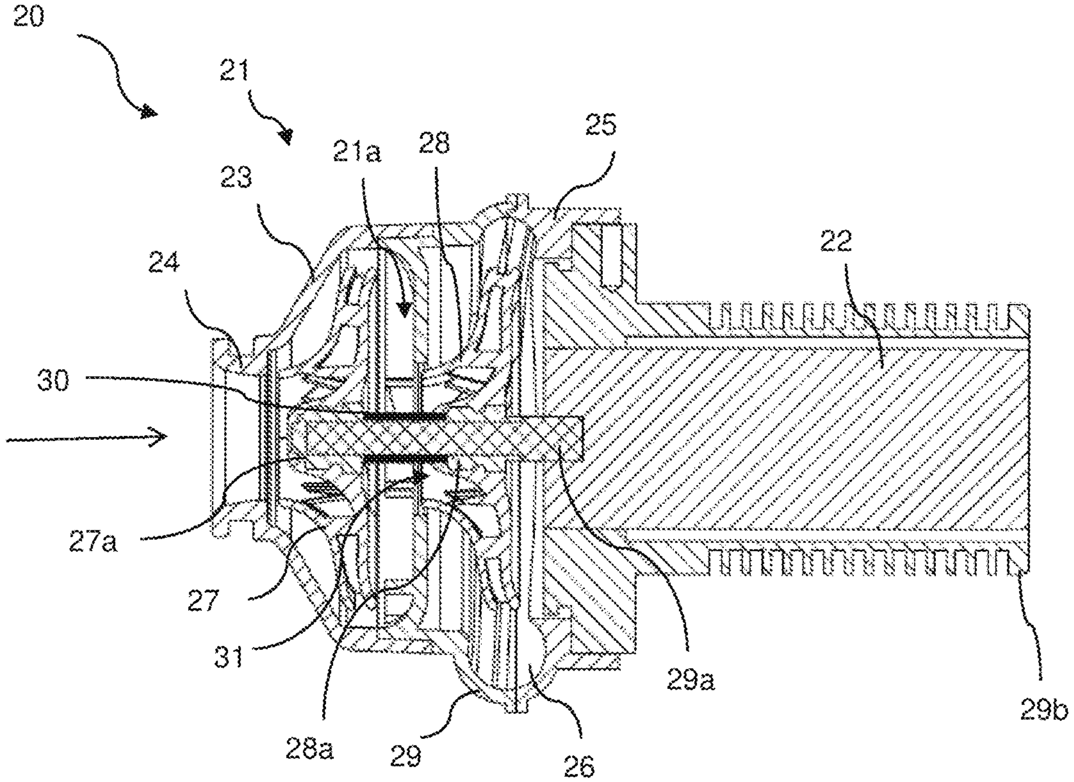
Prior Art FIG 2
FIG. 2 shows the blower apparatus according to FIG. 1 in a cross-sectional diagram.
Figure 3:
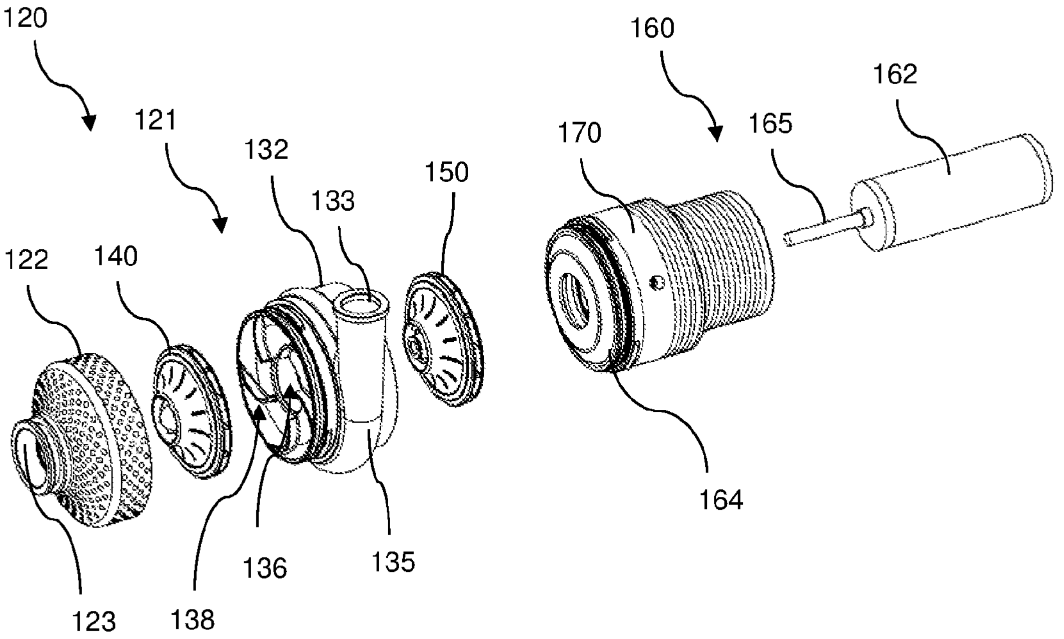
FIG. 3 shows a first embodiment of a blower apparatus according to the invention in an exploded diagram.
Figure 4:
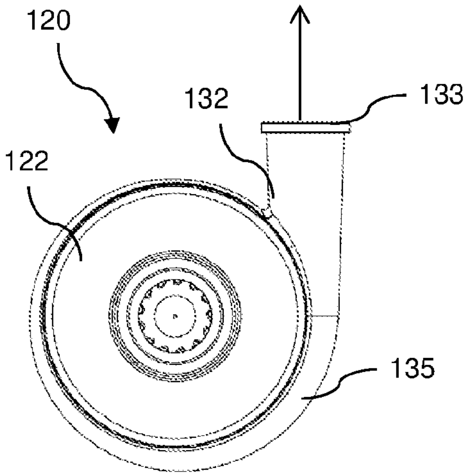
FIG. 4 shows the blower apparatus according to FIG. 3 in a plan view.
Figure 5:
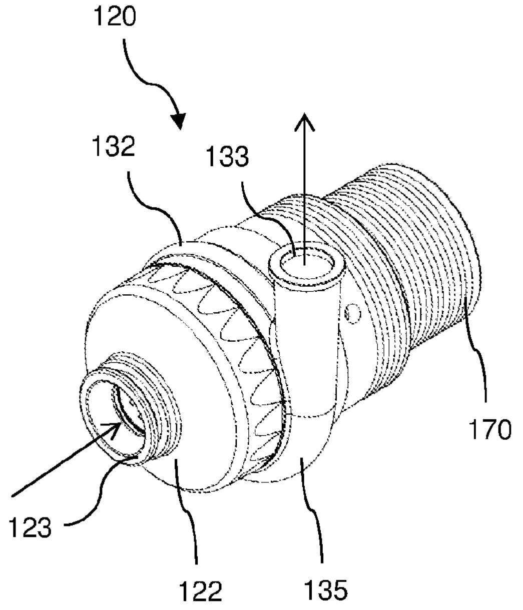
FIG. 5 shows the blower apparatus according to FIG. 3 in a further perspective diagram.

FIG. 1 and FIG. 2 show a known two-stage blower apparatus 20 from Micronel AG (CH) having a multi-part blower housing 21 consisting of a blower motor 22 and a first housing part 23. The first housing part 23 has a gas inlet 24. The blower housing 23 has a gas inlet 24. The blower housing 21 has a second housing part 25 which comprises the gas outlet 26 for the respiratory gas. Located between the first housing part 23 and the second housing part 25 is an intermediate housing 29 which is adhesively bonded to the first housing part 23 and the second housing part 25 and forms the gas outlet 26 in sections. The gas channel 21*a* in the multi-part blower housing 21 is formed by all three housing parts 23, 25, 29. Two blower wheels 27, 28 are arranged in the multi-part blower housing. The two blower wheels 27, 28 are spaced apart from one another and connected to respectively one fastening sleeve 27*a*, 28*a* with which the blower wheels 27, 28 are arranged on a motor shaft 29*a* of the blower motor 22. Located between the two blower wheels 27, 28 is a spacer sleeve 30 which extends through a housing opening 31 in the intermediate housing 29. The spacer sleeve 30 is arranged non-rotatably on the motor shaft 29*a*. The blower motor 22 is embraced by a heat sink 29*b* in sections.

The embodiments of the two-stage blower apparatus according to the invention which comprise a blower housing consisting of two housing parts are described subsequently. The two housing parts delimit the gas channel for the compressed respiratory gas with respect to the surroundings. The housing parts are produced by means of additive manufacturing methods (for example, according to VDI 3405).

FIG. 3 to FIG. 8 show a first embodiment of the two-stage blower apparatus 120 for a ventilator for providing a respiratory gas for a patient, having a multi-part blower housing 121. The multi-part blower housing 121 consists of a first housing part 122 and a second housing part 132, wherein a gas inlet 123 for the respiratory gas is provided on the first housing part 122 and a gas outlet 133 for the compressed respiratory gas is provided on the second housing part 132. The first housing part 122 and the second housing part 132 are connected to one another, wherein a gas channel 125 is formed from the first housing part 122 and from the second housing part 132. The gas channel 125 in the blower housing

121 is delimited with respect to the surroundings outside the two-stage blower apparatus 120 with the aid of the two housing parts 122, 132. A sealing unit 134, for example, an O ring, is provided on the second housing part 132 for positive connection of the two housing parts 122, 132.

The blower housing 121 forms a radial housing in sections, wherein the respiratory gas such as, for example, air or a gas mixture (air/oxygen/helium etc.), when used as intended, is sucked into the blower housing 121 through the gas inlet 123 and is compressed in the gas channel 125 to form a respiratory gas. The compressed respiratory gas is in this case moved along in the gas channel 125 of the blower housing 121 and leaves the blower housing 121 through the gas outlet 133 which is arranged at 90*o* relative to the gas inlet 123 on the second housing part 132. In this case, the compressed respiratory gas is moved radially in sections in the first housing part 122 and in the second housing part 132. The gas channel 125 has an outlet section 135 which is arranged completely on the second housing part 132.

The two-stage blower apparatus 120 has a first blower wheel 140 and a second blower wheel 150. The first blower wheel 140 is arranged in sections in the first housing part 122 and in sections in the second housing part 132. The second housing part 132 has a housing part opening 136 wherein a portion of the second blower wheel 150 extends through the housing part opening 136. The first blower wheel 140 rests in sections against the second blower wheel 150 and also extends in portion through the housing part opening 136. A spacer sleeve on the drive shaft between the two blower wheels 140, 150 can be dispensed with. Diffusor lamellae 138 are arranged on the second housing part 132, which are arranged adjacent to the first blower wheel 140 and extend axially towards the first blower wheel—see e.g. FIG. 3. The diffusor lamellae 138 form the gas channel 125 in sections.

Figure 6:
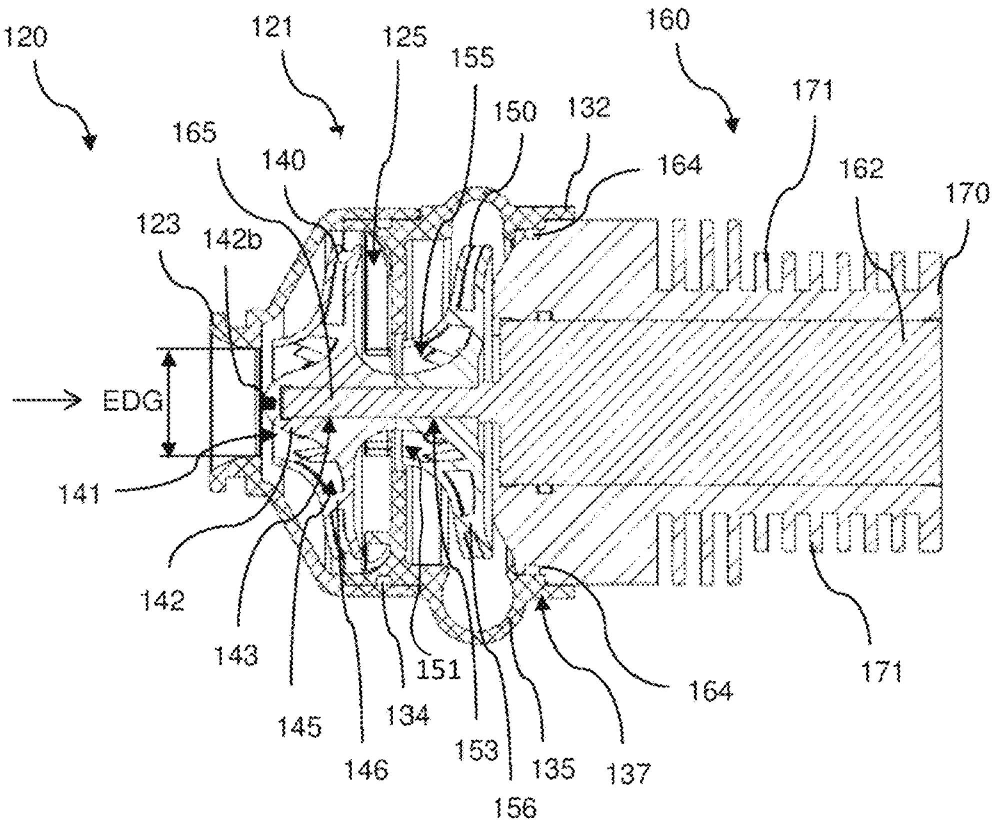
FIG. 6 shows the blower apparatus according to FIG. 3 in a further cross-sectional diagram.

As shown in detail in FIG. 6, a drive device 160 is provided for driving the two blower wheels 140 and 150, wherein the drive device 160 comprises a drive motor 162 and a drive shaft 165 which is driven by the drive motor 162. The drive device 160 is arranged adjacent to the second housing part 132, wherein the drive device 160 has a fastening section 164 for fastening the second housing part 132. The drive device 160 has a heat sink 170 with cooling fins 171, wherein the heat sink 170 encloses the drive motor 162. The second housing part 132 has a receiving section 137 for receiving the heat sink 170 in sections. The two blower wheels 140, 150 are arranged directly next to one another on the drive shaft 165, wherein the two blower wheels 140, 150 are shrunk on the drive shaft 165. The drive shaft 165 extends through the second blower wheel 150 and in sections through the first blower wheel 140.

Figure 7:
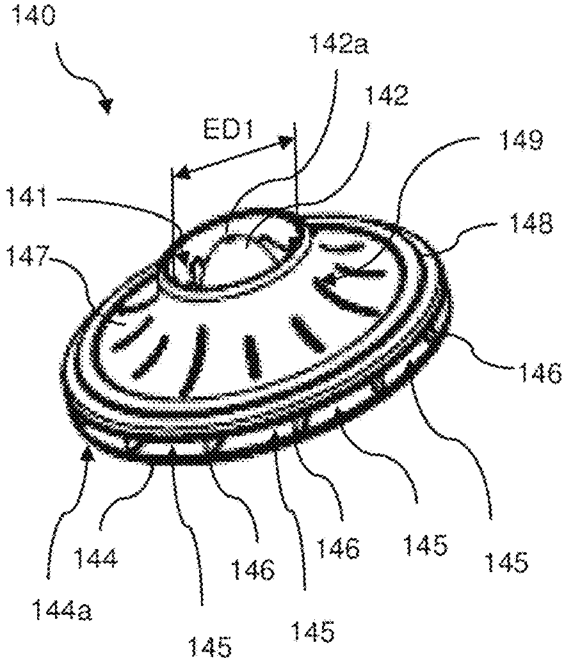
FIG. 7 shows a first blower wheel of the blower apparatus according to FIG. 3 in a perspective diagram.

FIG. 7 shows the first blower wheel 140 in detail. The first blower wheel 140 is one-piece and consists of polyamide. The first blower wheel 140 has an inlet opening 141 for the respiratory gas. When used appropriately, the respiratory gas is sucked from the surroundings into the gas inlet 123 of the first housing part 122 and further guided directly into the inlet opening 141 on the first blower wheel 140. The first blower wheel 140 comprises a bottom section 144 and a top section 147 with the inlet opening 141, wherein a plurality of blower lamellae 146 are arranged between the bottom section 144 and the top section 147 and thus a plurality of flow channels 145 with a plurality of blower lamellae 146 are formed. The inlet opening 141 of the first blower wheel 140 has an inlet diameter ED1 which is the same size as the minimum inlet diameter EDG of the gas inlet 123 of the first housing part 122. During use of the blower apparatus 120 as intended, the respiratory gas is compressed inside the first blower wheel 140 in a first compression stage with the aid of the blower lamellae 146 and leaves the blower wheel 140 at the blower wheel edges 144*a*.

The first blower wheel 140 has a spinner 142 which is arranged in the inlet opening 141 of the first blower wheel 140. The spinner 142 has a spinner opening 142*a*. The first blower wheel 140 has a fixing section 143 by means of which the blower wheel 140 is arranged on the drive shaft 165 of the drive motor 162. A closure element 142*b* is provided for closing the spinner opening 142*a*.

A balancing section 148 is arranged on the first blower wheel 140 on which the first blower wheel 140 is balanced either by means of the removal of material or by means of the supply of material. The balancing section 148 is arranged radially on the top section 147. Furthermore, a marking unit 149 is arranged on the first blower wheel 140 in order to simply determine the position of the first blower wheel 140 on the drive shaft 165 when balancing.

Figure 8:
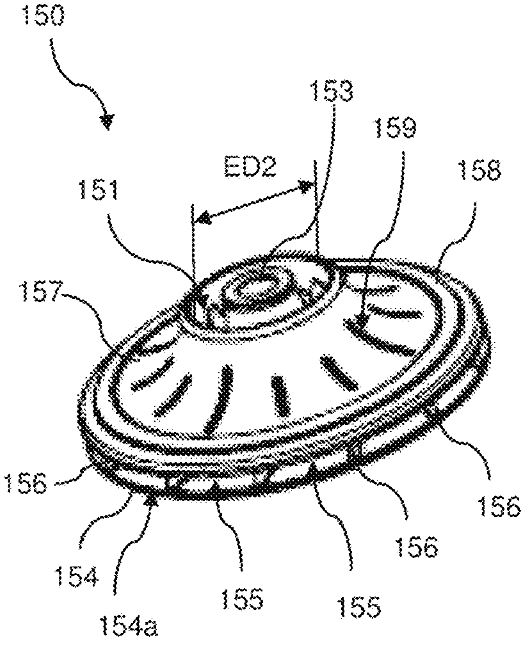
FIG. 8 shows a second blower wheel of the blower apparatus according to FIG. 3 in a perspective diagram.

FIG. 8 shows the second blower wheel 150 in detail. The second blower wheel 150 is one-piece and consists of polyamide. The second blower wheel 150 has an inlet opening 151 for the compressed respiratory gas. When used appropriately, after compression the respiratory gas is compressed with the aid of the first blower wheel 140 in the direction of the second blower wheel 150 and further guided directly into the inlet opening 151 on the second blower wheel 150. The second blower wheel 150 comprises a bottom section 154 and a top section 157 with an inlet opening 151, wherein a plurality of blower lamellae 156 are arranged between the bottom section 154 and the top section 157 and thus a plurality of flow channels 155 with a plurality of blower lamellae 156 are formed. The inlet opening 151 of the second blower wheel 150 has an inlet diameter ED2 which is the same size as the minimum inlet diameter EDG of the gas inlet 123 of the first housing part 122. During use of the blower apparatus 120 as intended, the respiratory gas is compressed inside the second blower wheel 150 in a second compression stage with the aid of the blower lamellae 156 and leaves the blower wheel 150 at the blower wheel edges 154*a*.

The second blower wheel 150 has a fixing section 153 with which the second blower wheel 150 is arranged on the drive shaft 165 of the drive motor 162.

A balancing section 158 is arranged on the second blower wheel 150 on which the second blower wheel 150 is balanced either by means of the removal of material or by means of the supply of material. The balancing section 158 is arranged radially on the top section 157. Furthermore, a marking unit 159 is arranged on the second blower wheel 150 in order to simply determine the position of the second blower wheel 150 on the drive shaft 165 when balancing.

Figure 9:
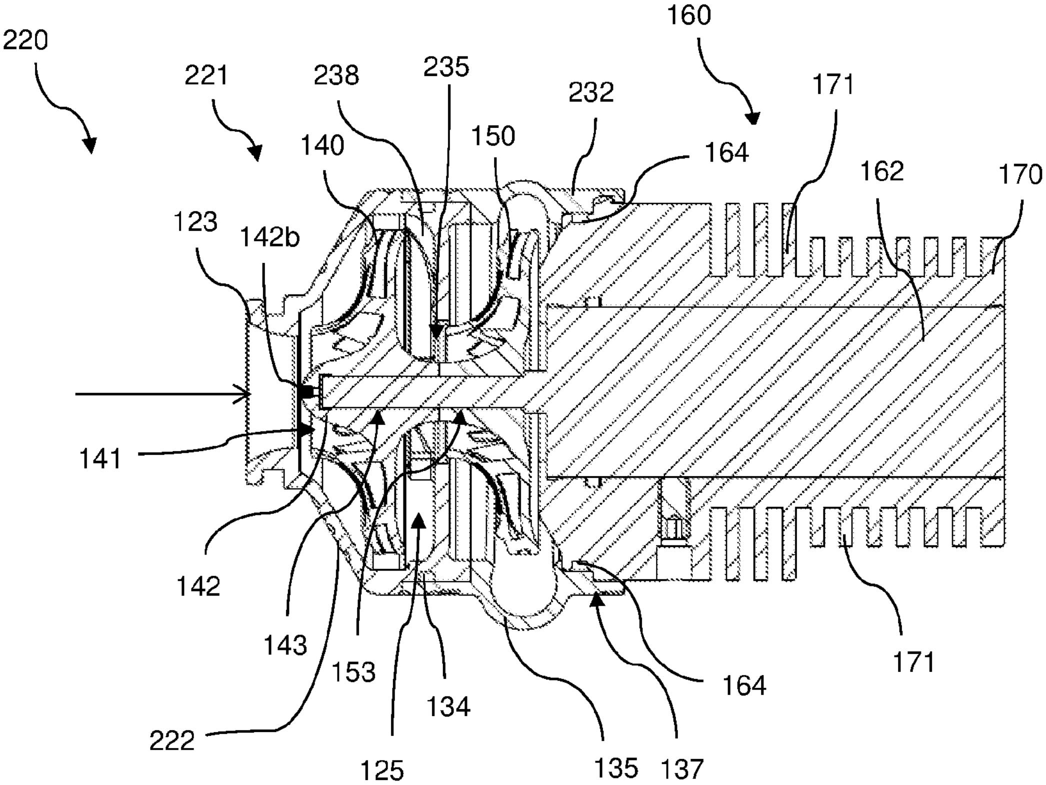
FIG. 9 shows a second embodiment of a blower apparatus according to the invention in a cross-sectional diagram.

FIG. 9 shows a second embodiment of a blower apparatus 220 according to the invention, wherein the blower apparatus 220 is constructed substantially functionally and structurally identically to the blower apparatus 120 according to FIG. 3 to FIG. 8. The blower apparatus 220 differs from the blower apparatus 120 only with regard to the configuration of the blower housing 221, the housing parts 222, 232 and therefore the arrangements of the two blower wheels 140, 150 in the housing parts 222, 232. The second blower wheel 150 is arranged in sections in the first housing part 222 and in sections in the second housing part 232. Diffusor lamellae 238 are arranged on the first housing part 222, which are arranged adjacent to the first blower wheel 140. The first housing part 222 has a housing part opening 235 wherein the second blower wheel 150 and the first blower wheel 140 extend in sections through the housing part opening 235. Alternatively to this, one of the two blower wheels 140, 150 extends through the housing part opening 235.

Figure 10:
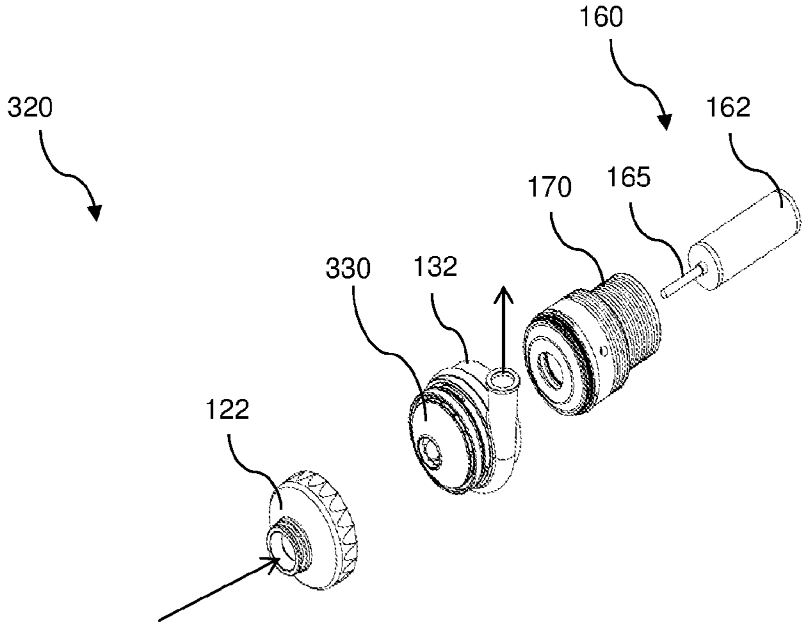
FIG. 10 shows a third embodiment of a blower apparatus according to the invention in an exploded diagram.
Figure 11:
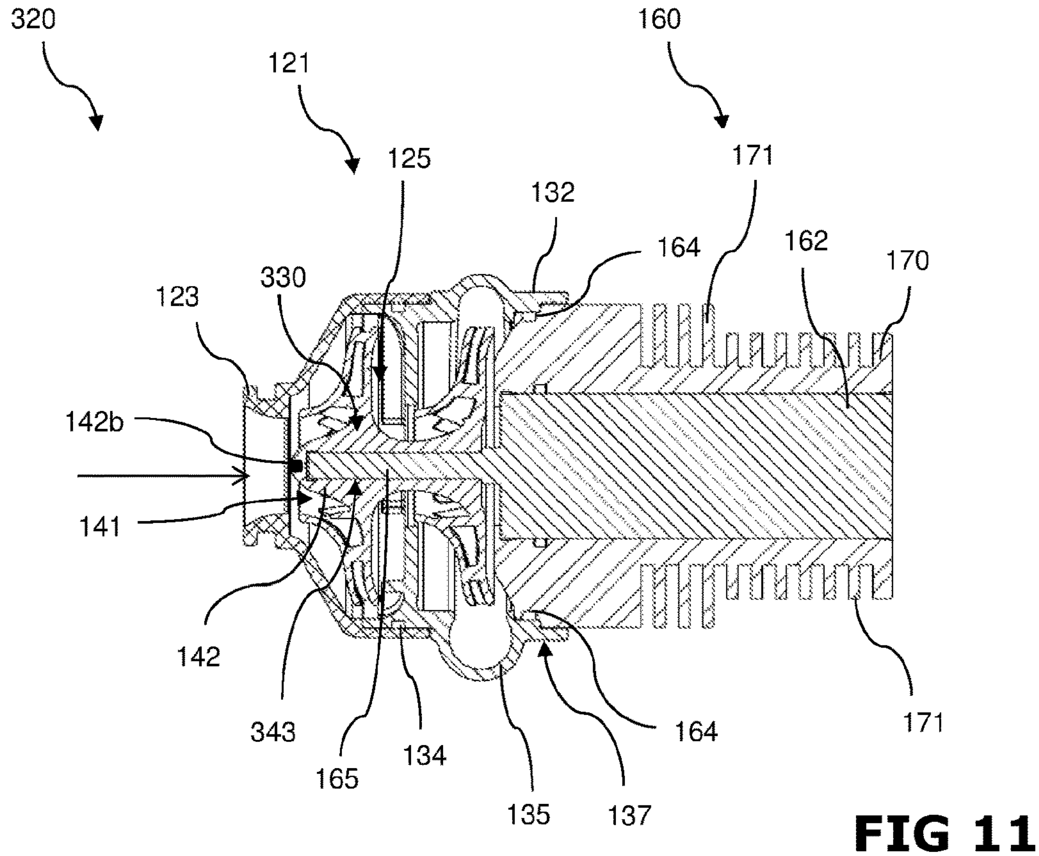
FIG. 11 shows the blower apparatus according to FIG. 10 in a cross-sectional diagram and FIG. 12 shows a further embodiment of a blower apparatus according to the invention in a cross-sectional diagram.

FIG. 10 and FIG. 11 show a third embodiment of a blower apparatus 320 according to the invention, wherein the blower apparatus 320 is constructed substantially functionally and structurally identically to the blower apparatus 120 according to FIG. 3 to FIG. 9. The blower apparatus 320 differs from the blower apparatus 120 only with regard to a one-piece blower wheel unit 330, which is formed from the blower wheels 140, 150. Thus, in the two-stage blower apparatus 320 there is no interface 125 between the two blower wheels 140, 150. The blower wheel unit 330 is integrated in the second housing part 132 and extends through the housing part opening 135, wherein the blower wheel unit 330 is produced with the aid of an additive manufacturing method. Otherwise, the blower wheel unit 330 comprises the structural and functional functions of the two blower wheels 140, 150 as described in FIG. 7 and FIG. 8. The blower wheel unit 330 is arranged with its fixing section 343 on the drive shaft 165. Such a blower wheel unit 330 can also be used in the blower apparatus 220 according to FIG. 9.

Figure 12:
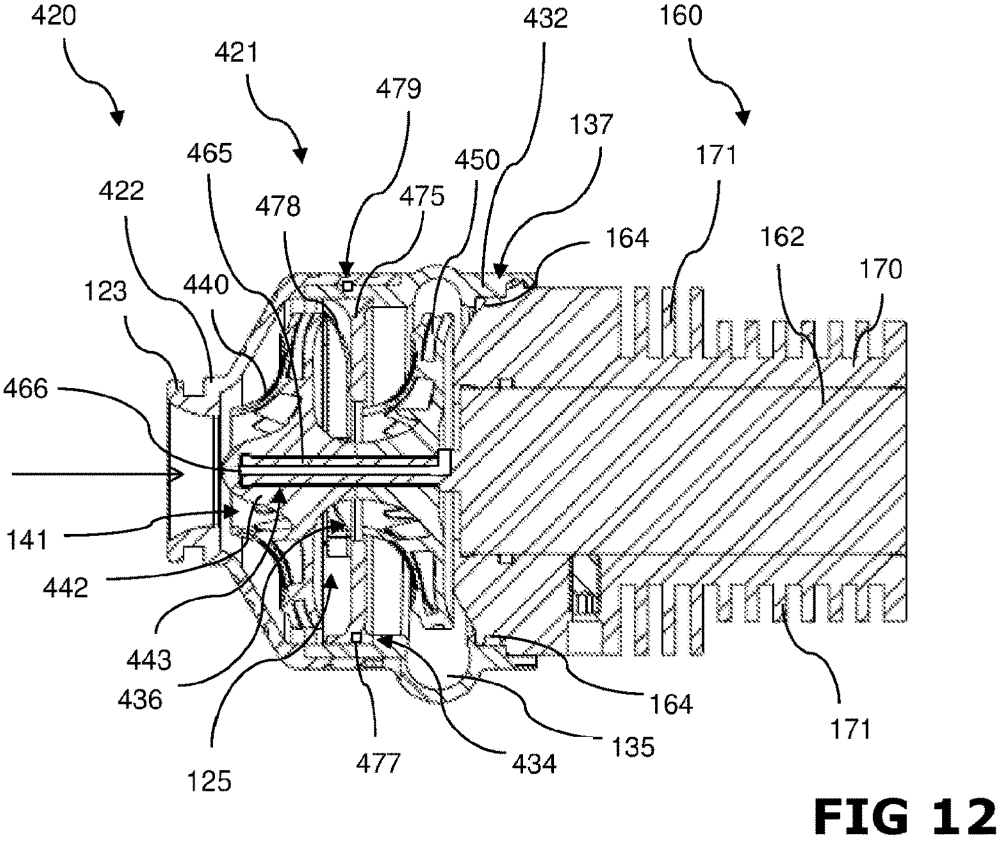

FIG. 12 shows a further embodiment of a blower apparatus 420 according to the invention, wherein the blower apparatus 420 is constructed substantially functionally and structurally identically to the blower apparatus 120 according to FIG. 3 to FIG. 9. The blower apparatus 420 differs from the blower apparatus 120 with regard to the first housing part 422 and the second housing part 432, wherein the second housing part has a receiving section 434 which is arranged inside the blower housing 421. The receiving section 434 accommodates a diffusor 475 with diffusor lamellae 478, which is arranged separably on the first and second housing part 422, 432. The diffusor 475 has a housing part opening 436, wherein at least one of the two blower wheels 440, 150 extends through the housing part opening 436 and the two housing parts 422, 432 are connected to one another. The diffusor 475 has a sealing unit 477 by means of which the diffusor 475 is connected sealingly on the second housing part 432. The first housing part 422 and the second housing part 432 are connected to one another by means of a snap closure 479. Alternatively or additionally, the first housing part has a receiving section for the diffusor (not shown).

In an alternative embodiment the blower apparatus 420 can also have a blower wheel unit 330 as shown in FIG. 11.

The blower apparatus 420 differs from the blower apparatus 120 with regard to the drive shaft 465 which has an axial bore 466 which opens into the spinner 442 of the first blower wheel 422. The axial bore 466 enables a simple arrangement of the drive shaft 465 on the fixing section 443 of the first blower wheel 422.

In an alternative embodiment, the blower apparatuses 120, 220, 320 can also have a drive shaft 465 and a spinner 442 according to FIG. 12.

A method according to the invention for producing a blower apparatus comprises an additive manufacture of the first housing part and/or the second housing part and/or the first blower wheel and/or the second blower wheel and/or the diffusor, of the blower apparatus 120, 220, 320, 420 described here in the present case.

REFERENCE LIST

20 Blower apparatus
21 Blower housing
21*a* Gas channel
22 Blower motor
23 First housing part
24 Gas inlet
25 Second housing part
26 Gas outlet
27 Blower wheel
27*a* Fastening sleeve
28 Blower wheel
28*a* Fastening sleeve
29 Intermediate housing
29*a* Motor shaft
29*b* Heat sink
30 Spacer sleeve
31 Housing opening of 29
120 Blower apparatus
121 Blower housing
122 First housing part
123 Gas inlet
125 Gas channel
132 Second housing part
133 Gas outlet
134 Sealing unit
135 Outlet section
136 Housing part opening
137 Receiving section
138 Diffusor lamellae
140 First blower wheel
141 Inlet opening
142 Spinner
142*a* Spinner opening
142*b* Closure element
143 Fixing section
144 Bottom section
144*a* Blower wheel edge
145 Flow channels
146 Blower lamellae
147 Top section
148 Balancing section
149 Marking unit
150 Second blower wheel
151 Inlet opening
153 Fixing section
154 Bottom section
154*a* Blower wheel edge
155 Flow channels
156 Blower lamellae
157 Top section
158 Balancing section
159 Marking unit
160 Drive device
162 Drive motor
164 Fastening section
165 Drive shaft
170 Heat sink
171 Cooling fins
220 Blower apparatus
221 Blower housing
222 First housing part
232 Second housing part
235 Housing part opening of 222
238 Diffusor lamellae
320 Blower apparatus
330 Blower wheel unit
343 Fixing section
420 Blower apparatus
421 Blower housing

422 First housing part
432 Second housing part
434 Receiving section on 432
436 Housing part opening
440 First blower wheel
442 Spinner
443 Fixing section
465 Drive shaft
466 Axial bore
475 Diffusor
477 Sealing unit
478 Diffusor lamellae
479 Snap closure
EDG Inlet diameter
ED1 Inlet diameter of 141
ED2 Inlet diameter of 151

The invention claimed is:

1. A two-stage blower apparatus for a ventilator for providing a respiratory gas for a patient, the two-stage blower apparatus comprising:
- a multi-part blower housing having a first housing part and a second housing part, wherein
  - a gas inlet for the respiratory gas is provided on the first housing part and,
  - a gas outlet for the respiratory gas is provided on the second housing part, and
  - a gas channel for the respiratory gas is formed in the first housing part and in the second housing part;
- a drive motor configured to rotate a drive shaft that extends through the second housing part and through at least a portion of the first housing part;
- a first blower wheel mounted to the drive shaft and at least partially within both the first housing part and the second housing part; and
- a second blower wheel mounted to the drive shaft and at least partially within the second housing part, wherein the first blower wheel lies against the second blower wheel.

2. The blower apparatus according to claim 1, wherein a drive device is provided for driving the first blower wheel and the second blower wheel, the drive device including the drive motor, the drive shaft, and a heat sink that and at least partially encloses the drive motor shaft.

3. The blower apparatus according to claim 1, wherein the first blower wheel and the second blower wheel each has at least one flow channel with a plurality of blower lamellae which form the gas channel, the first blower wheel and the second blower wheel each being constructed in one piece.

4. The blower apparatus according to claim 1, wherein
- the second housing part has a housing part opening; and
- at least one of the first blower wheel and the second blower wheel extends through the housing part opening.

5. The blower apparatus according to claim 1, wherein the first blower wheel has an inlet opening for the respiratory gas.

6. The blower apparatus according to claim 5, wherein the first blower wheel has a spinner which is arranged in the inlet opening of the first blower wheel.

7. The blower apparatus according to claim 6, wherein the drive shaft has an axial bore or a slot which opens into the spinner of the first blower wheel.

8. The blower apparatus according to claim 1, wherein the second blower wheel has an inlet opening for the respiratory gas.

9. The blower apparatus according to claim 1, wherein diffusor lamellae are arranged on the second housing part and are arranged adjacent to the first blower wheel.

10. The blower apparatus according to claim 1, wherein the first housing part and the second housing part are connected with a snap closure or a bayonet closure.

11. The blower apparatus according to claim 1, wherein the gas channel has an outlet section which is arranged completely on the second housing part.

12. The blower apparatus according to claim 1, wherein
- at least one of the first housing part and the second housing part is produced using additive manufacturing; and
- at least one of the first blower wheel and the second blower wheel is produced using additive manufacturing.

13. The blower apparatus according to claim 2, wherein at least one of the first blower wheel and the second blower wheel is shrunk on the drive shaft.

14. The blower apparatus according to claim 1, wherein the first blower wheel and the second blower wheel form a one-piece blower wheel unit.

15. The blower apparatus according to claim 5, wherein the inlet opening of the first blower wheel has an inlet diameter which is equal to a minimum inlet diameter of the gas inlet of the first housing part.

16. The blower apparatus according to claim 6, wherein the spinner has a spinner opening.

17. The blower apparatus according to claim 16, wherein a closure element is provided for closing the spinner opening.

18. The blower apparatus according to claim 8, wherein the inlet opening of the second blower wheel has an inlet diameter which is equal to a minimum inlet diameter of the gas inlet of the first housing part.

19. The blower apparatus according to claim 11, wherein the gas outlet for the respiratory gas is arranged at an angle of between 60° and 120° relative to the gas inlet.

20. The blower apparatus according to claim 18, wherein the gas outlet for the respiratory gas is arranged at an angle of 90° relative to the gas inlet.

* * * * *